United States Patent
Krall et al.

(10) Patent No.: US 6,476,069 B2
(45) Date of Patent: *Nov. 5, 2002

(54) COMPOSITIONS FOR CREATING EMBOLIC AGENTS AND USES THEREOF

(75) Inventors: Robert E. Krall, Alpine, CA (US); Charles W. Kerber, La Mesa, CA (US); Kimberly Knox, La Mesa, CA (US)

(73) Assignee: Provasis Therapeutics Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/241,368

(22) Filed: Jan. 29, 1999

(65) Prior Publication Data

US 2002/0098150 A1 Jul. 25, 2002

Related U.S. Application Data

(63) Continuation-in-part of application No. 09/151,621, filed on Sep. 11, 1998, now Pat. No. 6,037,366.
(60) Provisional application No. 60/058,510, filed on Sep. 11, 1997.

(51) Int. Cl.[7] .................. A61K 31/26; A61K 31/00; A61K 33/00; A61K 49/04; A61M 31/00
(52) U.S. Cl. .................. 514/527; 424/9.4; 424/9.42; 424/78.31; 424/78.35; 424/78.37; 424/422; 424/601; 424/605; 424/649; 424/667; 424/723; 514/526; 514/546; 514/558; 514/560; 514/718; 514/731; 514/970; 604/48; 604/500; 604/507; 604/514; 604/518
(58) Field of Search ............................ 424/9, 4, 9.42, 424/78.31, 78.34, 78.35, 78.37, 422, 649, 667, 723, 601, 605, 48, 500, 507, 514, 518; 514/772.3, 772.4, 772.6, 526, 527, 546, 558, 560, 718, 731, 970

(56) References Cited

U.S. PATENT DOCUMENTS

| | | | |
|---|---|---|---|
| 3,559,652 A | 2/1971 | Banitt | 128/334 |
| 3,692,752 A | 9/1972 | Setsuda et al. | 260/78.5 |
| 3,728,375 A | 4/1973 | Coover, Jr. et al. | 260/465.4 |
| 3,995,641 A | 12/1976 | Kronenthal et al. | 128/335 |
| 4,182,823 A | 1/1980 | Schoenberg | 526/298 |
| 4,313,865 A | 2/1982 | Toshio et al. | 524/753 |
| 4,321,180 A | 3/1982 | Kimura et al. | 524/549 |
| 4,328,170 A | 5/1982 | Okawara et al. | 260/465.4 |
| 4,359,454 A | 11/1982 | Hoffman | 424/5 |
| 4,713,235 A | 12/1987 | Krall | 424/5 |
| 5,403,591 A | 4/1995 | Tighe et al. | 424/445 |
| 5,530,037 A | 6/1996 | McDonnell et al. | 522/79 |
| 5,695,480 A | * 12/1997 | Evans et al. | 604/264 |
| 5,702,361 A | 12/1997 | Evans et al. | 604/508 |
| 5,703,267 A | 12/1997 | Takahashi et al. | 558/451 |
| 5,759,194 A | 6/1998 | Hammerslag | 606/214 |
| 5,795,331 A | 8/1998 | Cragg et al. | 604/103.01 |
| 5,981,621 A | * 11/1999 | Clark et al. | 523/118 |
| 6,037,366 A | * 3/2000 | Krall et al. | 514/527 |

FOREIGN PATENT DOCUMENTS

| | | |
|---|---|---|
| WO | WO 9707783 | 3/1997 |
| WO | WO 9942535 | 8/1999 |

OTHER PUBLICATIONS

Tseng et al., 'Modified ethoxyethyl cyanoacrylate for therapeutic embolization of arteriovenous malformation' (1990), Journal of Biomedical Materials Research, vol. 24, pp. 65–77.*

Woodward, 'Physiological and biochemical evaluation of implanted polymers' (Ann. N. Y. Acad. Sci. (1968), vol. 146, No. 1, pp. 225–250), STN/CAS online, file CAPLUS, Abstract.*

Barr et al., Microcatheter adhesion of cyanoacrylates: comparison of normal butyl cyanoacrylate ot 2–hexyl cyanoacrylate[1], *JVIR*, 10:1–6 (1999).

Connor & Wojack, "Future devices and procedures," *Interventional Neuroradiology. Strategies and Practical Techniques* W.B. Saunders Co., pp. 38–39 (1999).

Cromwell & Kerber, Modification of cyanoacrylate for therapeutic embolization: preliminary experience, *AJR*, 132:799–801 (1979).

Deburn et al., "Glued Catheters during embolisation of brain AVM's with acrylic glue" *Interventional Neuro.*, 3:13–19 (1997).

Gyurko et al., "Use in vascular surgery of the tissue adhesive histoacryl," *Acta Chir. Acad. Sci. Hung.* 15(4):353–360 (1974).

Mathis et al., "Hydrophilic coatings diminish adhesion of glue to catheter: an in vitro simulation of NBCA embolization" *Amer. J. Neuroradioal.*, 18:1087–1091 (1997).

Matsumoto et al. "Cyanoacrylate tissue adhesives: an experimental and clinical evaluation" *Milit. Med.* 134:247–252 (1969).

(List continued on next page.)

Primary Examiner—Jose' G. Dees
Assistant Examiner—Frank Choi
(74) Attorney, Agent, or Firm—Gray Cary Ware & Freidenrich LLP; Lisa A. Haile; Kelly K. Reynolds

(57) ABSTRACT

A composition useful as an embolic agent that selectively creates an embolic blockage in the lumen of a blood vessel, duct, fistula or other like body passageways by combining a monomer component and a second component wherein, said monomer component comprises of a alkyl cyanoacrylate monomer and at least one inhibitor agent; and said second component that functions as an opacificant agent and a polymerization retardant.

25 Claims, No Drawings

OTHER PUBLICATIONS

Tseng et al., "Modified ethoxyethyl cyanoacrylate for therapeutic embolization of arteriovenous malformation," *J. Biomed. Mater. Res.* 24:65–77 (1990).

Woodward, "Physiological and biochemical evaluation of implanted polymers" *Ann. N.Y. Acad. Sci.* 146(1):225–250 (1968).

Barr, John D., "Temporary and Permanent Occlusion of Cerebral Arteries," *Neuroendovascular Surgery*, vol. 11, No. 1, Jan. 2000, pp. 27–38.

Berthelsen, B. et al., "Embolization of Cerebral Arteriovenous Malformations with Bucrylate," *Acta Radiologica*, vol. 31, 1990, pp. 13–21.

Freeny, Patrick C. et al., "Transcatheter Therapy of Genitourinary Abnormalities Using Isobutyl 2–Cyanoacrylate (Bucrylate)," *AJR*, vol. 133, Oct. 1979 pp. 647–656.

Gobin, Dr. Y. Pierre et al., "Treatment of Brain Arteriovenous Malformations by Embolization and Radiosurgery," *J. Neurosurg*, vol. 85, 1996, pp. 19–28.

Halbach, Dr. Van V. et al., "Preoperative Balloon Occlusion of Arteriovenous Malformations," *Neurosurgery*, vol. 22, No. 2, 1988, pp. 301–308.

Kerber, Dr. Charles W. and Wong, Wade, "Liquid Acrylic Adhesive Agents in Interventional Neuroradiology," *Neuroendovascular Surgery*, vol. 11, No. 1, Jan. 2000, pp. 85–99.

Lefkowitz, Dr. Michael A. et al., "Balloon–assisted Guglielmi Detachable Coiling of Wide–necked Aneurysms: Part II—Clinical Results," *Neurosurgery*, vol. 45, No. 3, Sep. 1999, pp. 531–538.

Levy, Dr. David I., "Embolization of Wide–necked Anterior Communication Artery Aneurysm: Technical Note," *Neurosurgery*, vol. 41, No. 4, Oct. 1997, pp. 979–982.

Malek, Dr. Adel M. et al., "Balloon–assist Technique for Endovascular Coil Embolization of Geometrically Difficult Intracranial Aneurysms," *Neurosurgery*, vol. 46, No. 6, Jun. 2000, pp. 1397–1407.

Mericle, Robert A., M.D., "Temporary Balloon Protection as an Adjunct to Endosaccular Coiling of Wide–necked Cerebral Aneurysms", *Neurosurgery*, vol. 41, No. 4, Oct. 1997, pp. 1992–1998.

Moret, J et al., "The "Remodeling Technique" in the Treatment of Wide Neck Intracranial Aneurysms," *Interventional Neuroradiology*, vol. 3, 1997, pp. 21–35.

Pelz, David M. et al., "Preoperative Embolization of Brain AVMs with Isobutyl–2 Cyanoacrylate," *AJNR*, vol. 9, Aug. 1988, pp. 757–764.

Rao, V.R.K. et al., "Dissolution of Isobutyl 2–Cyanoacrylate on Long–Term Follow–Up," *AJNR*, vol. 10, Jan./Feb. 1989, pp. 135–141.

Spiegel, S. M. et al., "Adjusting the Polymerization Time of Isobutyl–2 Cyanoacrylate," *American Journal of Neuroradiology*, vol. 7, Jan./Feb. 1986, pp. 109–112.

Vinuela, F.V. et al., "Dominant–Hemisphere Arteriovenous Malformations: Therapeutic Embolization with Isobutyl–2–Cyanoacrylate," *AJNR*, vol. 4, Jul./Aug. 1983, pp. 959–966.

Vinuela, Fernando et al., "Progressive Thrombosis of Brain Arteriovenous Malformations After Embolization with Isobutyl 2–Cyanoacrylate," *AJNR*, vol. 4, Nov./Dec. 1983, pp. 1233–1238.

Vinuela, Fernando et al., "Angiographic Follow–Up of Large Cerebral AVMs Incompletely Embolized with Isobutyl–2–Cyanoacrylate," AJNR, vol. 7, Sep./Oct. 1986, pp. 919–925.

* cited by examiner

COMPOSITIONS FOR CREATING EMBOLIC AGENTS AND USES THEREOF

RELATED APPLICATIONS

The present application is a continuation in part of U.S. application serial No. 09/151,621, filed on Sep. 11, 1998, now issued U.S. Pat. No. 6,037,366, which claims priority under 35 U.S.C, §119 to U.S. ProvisionAl Application Serial No. 60/058,510, filed on Sep. 11, 1997, now abandoned, both of which are hereby incorporated by reference in their entirety.

FIELD OF THE INVENTION

This invention relates to cyanoacrylate polymer compositions useful as medical devices.

BACKGROUND OF THE INVENTION

Cyanoacrylate tissue adhesives have been in clinical endovascular use since the 1970's. Liquid acrylics are extremely useful as endovascular embolic agents because of their ability to create permanent vascular occlusion. They may, however, be difficult to use technically as they have a variable and sometime unpredictable polymerization time based on the operator selection of an acrylic mix with either iodinated oil or glacial acetic acid. The appropriate choice of polymerization time depends on a number of variables, including the transit time between arterial and venous elements in the embolic target, the target volume, the architecture of the target, for example, a fistula versus nidus, which affects the relative endovascular turbulence, and the method of injection (bolus, full column, or wedge-flow arrest). Typical complications associated with the use of liquid acrylics for embolization occur when there is occlusion of normal arterial branches or acrylic penetration into critical venous outflow channels. Additionally, reflux of acrylic around the delivery catheter tip can result in permanent endovascular catheter adhesion, which may require permanent catheter implantation. Overzealous attempts at withdrawal can produce catheter fracture (and resultant embolization of flow-directable distal catheter segment), vascular damage with resultant dissection/occlusion, or avulsion of the involved vascular pedicle (with resultant subarachnoid hemorrhage).

Alkyl alpha cyanoacrylates are a homologous series of organic molecules which polymerize and can adhere to moist living tissues. The methyl homolog has been used in hemostasis and non-suture closure since 1960, but its histoxicity severely limited its clinical usefulness. The synthesis of longer alkyl chain homologs and the evaluation of these in various animal species have shown that the histoxicity of cyanoacrylates could be diminished without sacrificing their hemostatic and tissue bonding properties. Extensive animal studies have been completed using n-butyl and isobutyl homologs, and preliminary human trials have been undertaken.

Polymerization speed is another function of chain length. It has been reported that homologs with six or more carbon atoms on the alkyl chain polymerize almost immediately upon contact with moist tissues. The n-butyl and isobutyl monomers require from four to 15 seconds, while the methyl homolog remains as a monomer for 30 to 55 seconds. The ability to wet and spread easily over the surface of an anticoagulated blood film is common to homologs with alkyl chains containing four or more carbon atoms. The ethyl and propyl derivatives wet and spread poorly, and the methyl not at all.

Since the advent of NBCA (n-butyl-2-cyanoacrylate), there has been very little advancement in the science of "superglue" embolization of vascular structures, primarily arteriovenous malformations (AVMs). Certain properties of superglue are advantageous for embolization, such as adhesion, the ability transform from a liquid or solid state and rapid polymerization. However, these properties can be detrimental when present to an excessive degree, in particular, adhesion which can result in permanent catheter fixation. Rapid polymerization allows the material to set in flowing blood without passing through small channels into venous structures. However, rapid polymerization may also release amounts of heat that can cause damage to the surrounding tissue, for example, brain tissue.

Hydrophilic catheter coatings have been developed in the hope of which reduce the risk of inadvertent endovascular catheter fixation during embolization due to reduced bond strength between the hydrophililically coated catheter and the adhesive. However, microcatheter cyanoacrylate adhesion remains a problem during intravascular embolization. Inadvertent gluing of the catheter tip onto the artery is a well recognized and distressing complication. Vessel rupture or occlusive embolization of a detached catheter tip may occur if excessive force is used to attempt to retrieve the catheter. Fortunately, permanent intravascular catheter fixation is usually well tolerated, nonetheless this remains a highly undesirable event. An in vitro study has shown that recently available hydrophilic microcatheter coatings decrease catheter adhesion of both pure normal butyl cyanoacrylate and mixtures of normal butyl cyanoacrylate and ethiodized oil. Although hydrophilically coated catheters have the potential of decreasing the occurrence of inadvertent endovascular catheter fixation, the level of operator proficiency and experience, and perhaps most importantly, the actual adhesive composition that is used stills play a major role in these events.

There exists a continuing unmet need for a composition that has the correct amount of cohesiveness, produces a robust rubbery casting, is tolerated by the body, can trigger the appropriate amount of tissue inflammation response and is radiopaque.

It has now been surprisingly found that such a composition exists that has the requisite combination of properties in cohesion, stability, body tolerance, low catheter adhesion and radiopacity.

SUMMARY OF THE INVENTION

A composition useful as an embolic agent that selectively creates an embolic blockage in the lumen of a blood vessel, duct, fistula or other like body passageways by combining a monomer component and a second component wherein, said monomer component comprises of a alkyl cyanoacrylate monomer and at least one inhibitor agent; and said second component that functions as an opacificant agent and a polymerization retardant.

DETAILED DESCRIPTION OF THE INVENTION

The present invention provides a composition useful as an embolic agent that selectively creates an embolic blockage in the lumen, either totally or partially, of a blood vessel, duct, fistula or other body passageways by combining a monomer component and a second component where the monomer component comprises of a alkyl cyanoacrylate monomer and at least one inhibitor agent; and the second component functions as an opacificant agent and a polymerization retardant.

One embodiment of the present invention is where the second component is Ethiodol.

Another embodiment of the present invention is a composition useful as an embolic agent that selectively creates an embolic blockage in the lumen of a blood vessel, duct, fistula or other like body passageways by combining a monomer component and a second component where the monomer component comprises of a alkyl cyanoacrylate monomer and at least one inhibitor agent; and the second component comprises, a polymer resulting from the alkyl cyanoacrylate monomer, a alkyl esterified fatty acid and an opacificant agent. In particular, where the monomer component comprises of 2-hexyl cyanoacrylate monomer, hydroquinone, p-methylphenol and phosphoric acid; and the polymer component comprises of 2-hexyl cyanoacrylate polymer, gold, and ethyl myristate.

Ethyl myristate, other fatty acid esters, subbicates, and other plasticizers, are useful for fastening the polymers of the cyanoacrylates. See U.S. Pat. No. 6,037,366 (which has been incorporated herein in its entirety), Column 3, lines 45–52, Column 4, lines 1, 2.

Another embodiment of the present invention provides a method for selectively creating an embolic blockage in the lumen of a blood vessel, duct, fistula or other like body passageways.

Another embodiment of the present invention provides a method of treating arteriovenous malformation (AVM).

Definitions

As used herein the terms "adhesion" or "adhesive" means the characteristic or tendency of a material to be attracted to the surface of a second material. Adhesion occurs as the result of interacts between two materials. Depending on the characteristics of the second material relative to the first material, adhesion may or may not occur. For a single material, e.g., the composition of the present invention, the presence of adhesion is demonstrated by a material sticking to the wall of a lumen of blood vessel, i.e., there is adhesion between the material and the lumen wall. Conversely, the absence of adhesion is demonstrated for the same material where a micro-catheter tip used to deposit the material can be removed from the material, i.e., there is no adhesion between the material and micro-catheter tip.

As used herein the term "cohesion" or "cohesive" means the characteristic or tendency of a material to stick together to itself. For example, this characteristic is demonstrated by a material or composition remaining intact as a single mass when introduced into a stationary fluid, or a fluid stream in motion, such as, blood. Lack of cohesive integrity results in the composition breaking up into multiple smaller subunits.

As used herein the term "embolic agent" refers to a non-naturally occurring composition introduced into a body cavity for the purpose of forming an embolic block.

As used herein the term "embolic block" or "embolic blockage" refers to the end result from administering an embolic agent, that is where a man-made composition mechanically blocks, totally or partially, the lumen of a blood vessel, duct, fistula or other like body passageways.

As used herein the term "alkyl cyanoacrylate monomer" means chemical of the general structure $H_2C=C(CN)—C(O)O—R$, where R is a alkyl moiety of one to sixteen carbon atoms, linear or branched, saturated or unsaturated.

As used herein the term "alkyl cyanoacrylate polymer" means an oligomer or polymer resulting from the polymerization of a alkyl cyanoacrylate monomer.

As used herein the term "alkyl esterified fatty acid" means a fatty acid derivatized to form an ester functional group with a alkyl moiety, such as ethyl myristate, and group of compounds formed with an alkyl moiety, such as methyl, ethyl, propyl, butyl, pentyl, hexyl, heptyl, and octyl; and carboxylic acids with aklyl side chains ranging from 1 carbon, i.e., acetic acid, through to and including 17 carbons atoms in length, such as, proprionic, butyric, isobutyric, valeric, isovaleric, pivalic, lauric, myristic, palmitic and stearic acids.

As used herein the term "opacificant agent" is compound or composition which selectively absorbs or deflects radiation making the material visible under x-ray, or any like imaging technique. Typically such agents include, iodinated oils, and brominated oils, as well as commercially available compositions, such as Pantopaque, Lipiodol and Ethiodol. These commercially available compositions acts as opacificant agents, and also dilute the amount of liquid monomer thereby slowing the rate of polymerization.

As used herein the term "polymerization" refers to the chemical process where identical monomer units react chemically to form larger aggregates of said monomeric units as oligomers or polymers.

As used herein the term "polymerization retardant" means an agent that can stop or slow down the rate of polymerization. Examples of such agents are pure phosphoric acid, and 85% phosphoric acid. Certain opacificant agents, such as Pantopaque, Lipiodol and Ethiodol can also function as a polymerization retardant by diluting the amount of liquid monomer and hence slowing polymerization rate.

As used herein the term "stability" refers to the ability of a monomer component to resist degradation or polymerization after preparation but prior to use.

As used herein the term "inhibitor agent" refers to an agent which stabilizes a monomer composition by inhibiting polymerization. Within the context of the current invention, this term refers to agents that stabilize and inhibit polymerization by various mechanism. By altering the amounts of one or more inhibitor agents, the rate of polymerization can be controlled. Inhibitor agents have different modes of activity, for example, hydroquinone acts primarily to inhibit high energy free radicals; p-methoxyphenol acts primarily to inhibit low energy free radicals; and phosphoric acid influences the rate of anionic polymerization.

Nomenclature

The compound 2-hexyl cyanoacetate is depicted as follows, and also as Formula 3 in Schemes A and B.

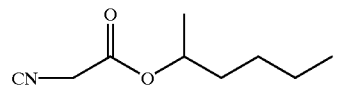

The compound 2-hexyl cyanoacrylate is depicted as follows, and also as Formula 5 in Scheme B.

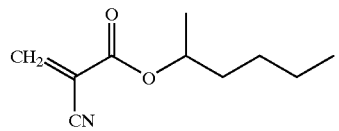

The present invention is a composition formed from alkyl cyanoacrylate monomeric units, such as, n-butyl, 1-isobutyl and 2-hexyl cyanoacrylate with at least one inhibitor, such as hydroquinone, p-methoxyphenol and phosphoric acid. The composition forms into its resultant aggregate structure, i.e., an oligomer or polymer, when it comes in contact with an anionic solution, such as, blood. The resultant aggregate composition has characteristics which makes it particularly well suited as an embolic agent.

The composition of the present invention possess the following properties, which are desirable in an embolization agent.

1) The composition can be prepared and maintained as a monomeric component and second component until needed.
2) The composition has the ability to reliably and predictably change from a liquid state to a solid state, which is essential for its introduction and controlled placement into the lumen of vessel, duct, fistula or other like body passageways.
3) The composition has low viscosity, which is essential for its administration by syringes and micro-catheters or other like devices.
4) The composition has cohesive characteristics such that when the composition in administered into an anionic fluid environment, such as blood, the composition forms a single aggregate structure.
5) The composition has adhesive characteristic such that it attaches to the lumen of vessel, duct, fistula or other like body passageways, but not to the degree where the device depositing the composition will become fixed to it before the practitioner can remove it.
6) The composition causes mild tissue inflammation, sufficient to cause scarring, but not so severe to cause the formation of pus. Scar formation is necessary to maintain the functionality of the embolic block after the composition has biodegraded, or otherwise eliminated from the lumen.
7) The composition is sufficiently stable to biodegradation to allow for scarring to occur.
8) The composition is radiopaque. Although not necessary for its function as an embolic agent, radiopacity allows the embolic block to be observed with x-ray or other such imaging techniques.
9) The rate of heat released during polymerization of the composition is low enough such that the heat does not adversely effect surrounding tissues that may be heat sensitive, such as brain tissue.
10) The composition and its biodegradation products are sufficiently non-histotoxic and non-cytotoxic so that its presence is well tolerated in the body.

The composition of the present invention is used by combining the monomer component and second component. Upon mixing of the components, the invention is administered into the lumen of a blood vessel, duct, fistula or other like body passageways. The characteristics of the present invention permit its accurate placement in the lumen. Contact with an anionic fluid, such as blood, causes the composition to polymerize. The size of the resultant embolic block formed is determined by the amount of composition administered.

The characteristics of the composition of the invention can be modified for a specific purpose or environment for which the embolic agent is intended to be utilized. For example, changes in the length and isomeric configuration of the alkyl side chains can alter the brittleness of the resultant aggregate of cyanoacrylate monomers. Alkyl chains that result in the formation of smaller aggregates tend to be more brittle, while larger aggregates tend to be more flexible.

Cyanoacrylates generate heat as they change from monomeric to polymeric form. The amount and rate of heat released, if excessive, can have a detrimental effect on the living tissue proximate to the vessel. Control of the amount and rate at which heat is release during polymerization is critical to the utility of composition.

Preparation of the Monomer Component

The monomer component of the present invention is prepared by forming the desired precursor ester from the corresponding alkyl alcohol and cyanoacetic acid resulting in the desired alkyl cyanoacetate as depicted in Scheme A. The starting materials for this reaction are commercially available, for example from Alrich Chemical Company, Sigma Chemical Company or Fluka Chemical Company, or can be prepared following procedures known to those of ordinary skill in the art.

Scheme A

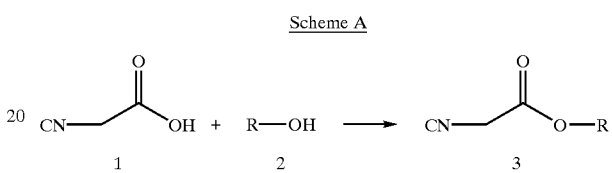

The compound of Formula 2 can be any alkyl alcohol, where R is from one to sixteen carbons, including but not limited to alcohols based on alkyl groups, such as, methyl, ethyl, propyl, butyl, pentyl, hexyl, heptyl, heptyl, octyl, nonyl, deca, undeca, dodeca, trideca, tetradeca, pentadeca and hexadeca, where the preceding moieties are linear (e.g., n-propyl, n-butyl, n-pentyl) or variously branched, such as sec-butyl, iso-butyl, tert-butyl, iso-propyl, 2-butyl, 2-pentyl, 2-hexyl, 2-heptyl, 2-octyl and the like. Particularly advantageous alcohols are those disclosed in U.S. Pat. No. 3,728,375 entitled "Cyanoacrylate Adhesive Compositions", which is hereby incorporated by reference. Especially preferred are n-butyl, iso-butyl and 2-hexyl alcohols.

About 1 molar equivalents of the compounds of Formula 1 and Formula 2 are combined in a solvent like toluene at about 100 ml/molar equivalents. To this mixture is added a small quantity (about $1.0 \times 10^{-4}$ molar equivalents) of p-toluene sulfonic acid. The mixture is stirred and heated to reflux. The preparation ideally yields the desired alkyl cyanoacetate at a purity level of about 95%. The experimental conditions can be readily modified by one of ordinary skill in the art without deviating from the present invention. Aspects such as, solvent selection, reaction time, temperature and choice of reagents are well within the skill of one of ordinary skill in the art. If necessary, the material can be further purified using multiple distillations and purification techniques and procedures known to those of ordinary skill in the art, such as water extraction, vacuum distillation, column chromatography, preparative gas chromatography and the like.

Preparation of Alkyl Cyanoacrylate

The desired alkyl cyanoacrylate monomer component of the present invention is synthesized from the alkyl cyanoacetate by reacting the it in a Knöevengel type reaction as depicted in Scheme B.

Scheme B

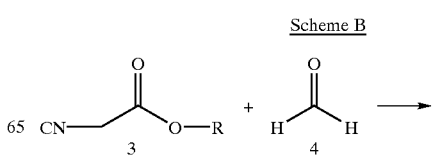

-continued

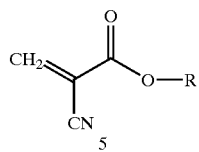

About 1 molar equivalents of formaldehyde (Formula 4), which is prepared from paraformaldehyde, and piperidine (at about 0.33 ml/molar equivalents) are combined in a solvent, such as methanol (at about 166 ml/molar equivalents). To this mixture is added about 1 molar equivalents of previously prepared alkyl cyanoacetate (Formula 3) in a dropwise manner. The reaction mixture is refluxed with stirring yielding the desired alkyl cyanoacrylate polymer (Formula 5). The reaction mixture is further processed with about 0.56 to 0.7 molar equivalents of phosphorous pentoxide yielding the desired alkyl cyanoacrylate. Care must be taken during purification steps to prevent the compound of Formula 5 from polymerizing. To this end the system is treated with trace amounts of sulfur dioxide, and receiver flasks are treated with hydroquinone and 85% phosphoric acid. After initial purification, the desired alkyl cyanoacrylate is further purified using multiple distillations, or other purification techniques known to those of ordinary skill in the art, such as vacuum distillation, spinning band column, HPLC and the like.

Formulation

The monomer component comprises of the alkyl cyanoacrylate and at least one inhibitor agent. Typical inhibitors appropriate for cyanoacrylates are, for example, hydroquinone, p-methoxyphenol, pure phosphoric acid, and alkyl carboxylic acids, where the alkyl moiety ranges from 1 carbon, i.e., acetic acid, through to 15 and 17 carbons atoms in length, i.e., palmitic and stearic acids, respectively; and phosphoric acid at varying percentage solutions, preferably hydroquinone, p-methoxyphenol and phosphoric acid are used, individually or in combination.

Different inhibitors have different physical characteristics and thereby functions to alter the final properties of the composition. For example, hydroquinone is primarily an inhibitor for high energy free radicals; p-methoxyphenol is primarily an inhibitor for low energy free radicals; and phosphoric acid acts to control or inhibit anionic polymerization and the rate of such polymerization.

The quantity of inhibitors used is measured in terms of parts per million of alkyl cyanoacrylate. For example, for 2-hexyl cyanoacrylate, hydroquinone is in the range of about 50 to 150 parts per million (PPM), p-methoxyphenol in the range of about 50 to 150 PPM, and phosphoric acid in the range of about 125 to 375 PPM, more preferred is hydroquinone in the range of about 75 to 125 PPM, p-methoxyphenol in the range of about 75 to 125 PPM, and phosphoric acid in the range of about 187.5 to 312.5 PPM, and most preferred is hydroquinone in the range of about 95 to 105 PPM, p-methoxyphenol in the range of about 95 to 105 PPM, and phosphoric acid in the range of about 200 to 300 PPM.

The second component functions as an opacificant agent and a polymerization retardant. To this end, the second component can be an iodinated oil, (such as Ethiodol) or a brominated oil. Typically the iodinated oil is mixed as some percent of the total volume of the final composition. The percentage solution of iodinated oil used will influence the polymerization rate and opacity of the composition. Generally advantageous ranges are from about 17% to 66%, preferably about 33%.

Alternatively, the second component can be a composition comprising, a opacificant material, such as gold, platinum, tantalum, titanium, tungsten and barium sulfate and the like, blended together with alkyl cyanoacrylate polymer material, and an esterified fatty acid, such as ethyl myristate. The opacificant element or material is used in a fine powder form, typically, with individual particles sized no larger than about 7 microns in diameter, preferably about 5 microns, most preferred about 2 microns or smaller.

The amount of opacificant material relative to alkyl cyanoacrylate polymer will varying according to the specific materials. Factors that influence the determination of the ratio include the amount and size of the particles that are being coated by the alkyl cyanoacrylate polymer. For example, for 2-hexyl cyanoacrylate and gold, 2 g of 2-hexyl cyanoacrylate is used per 100 g of powdered gold (particle size of about 5±2 microns) being coated. The amount varies accordingly with the opacificant material being coated by the alkyl cyanoacrylate. The alkyl cyanoacrylate and opacificant material are mechanically mixed by processing the alkyl cyanoacrylate into small particulate masses, and mixing with the finely powdered opacificant material. The alkyl cyanoacrylate polymer coated material is then stored in an esterified fatty acid, which serves as a medium where the aklyl cyanoacrylate polymer coated material is maintained prior to use, and as a medium, which when contacted with the monomer component will not interfere with the polymerization of the composition. The unsealed storage containers, preferably appropriately sterilized bottles and caps or the like, with the cyanoacrylate polymer suspension is then treated with ethylene oxide, or alternatively ketene. This treatment should occur no later than about 48 hours after completion of the coating process, preferably within 24 hours. The treatment process provides sterilization and stabilization of the alkyl cyanoacrylate polymer coated material and follows standard procedures for ethylene oxide use, i.e., positioning the contains so that they are amply exposed to the gas for a sufficient period of time.

Utility

The present invention is useful as an embolic agent that selectively creates an embolic blockage in the lumen of a blood vessel, duct, fistula or other like body passageways.

The present invention can be prepared and maintained as a monomeric component and second component until needed. It has the ability to reliably and predictably change from a liquid state to a solid state, which is essential for its introduction and controlled placement into the lumen of vessel, duct, fistula or other like body passageways. The composition has low viscosity, which is essential for its administration by syringes and micro-catheters or other like devices.

The cohesive characteristics of the invention are such that when the composition in administered into an anionic fluid environment, such as blood, the composition forms a single aggregate structure. Additionally, the has adhesive characteristics are such that the composition attaches to the lumen of vessel, duct, fistula or other like body passageways, but not to the degree where the device depositing the composition will become fixed to it before the practitioner can remove it.

The present invention causes mild tissue inflammation, sufficient to cause scarring, but not so severe to cause the formation of pus. Scar formation is desirable as the scar tissue is necessary to maintain the functionality of the embolic block after the composition has biodegraded, or otherwise eliminated from the lumen. The composition is sufficiently stable to biodegradation to allow for scarring to occur.

The present invention is radiopaque. Although this characteristic is not necessary for its function as an embolic agent, radiopacity allows the embolic block to be observed with x-ray or other such imaging techniques.

The rate of heat released during polymerization of the present invention is low enough such that the heat does not adversely effect surrounding tissues that may be heat sensitive, such as brain tissue.

The present invention and its biodegradation products are sufficiently non-histotoxic and non-cytotoxic so that its presence is well tolerated in the body.

The present invention is an embolic agent that provides a method for selectively creating and placing an embolic blockage which mechanically blocks, totally or partially, the lumen of a blood vessel, duct, fistula or other body passageway. In particular, the current invention is particularly useful in blocking, totally or partially, or diverting the flow of blood through the lumen.

The present invention can be advantageously used to block blood flow to certain tissues or areas. For example, the present invention can be used to treat arteriovenous malformation (AVM). An AVM is a collection of abnormal blood vessels which are neither arteries or veins. These vessels are packed closely together to form the nidus of the AVM. Blood flow into the AVM nidus is through thinned, enlarged, tortuous vessels and is rapidly shunted into draining veins because the nidus contains no arterioles or capillaries to provide high resistance. Clinical symptoms experienced because of AVMs are bleeding, re-direction of blood from nearby normal structures, or seizures. The primary clinical problem associated with cerebral AVM is the potential for lethal hemorrhage. The current standard of care for treating AVMs is surgical removal, high energy radiation or embolization with particular devices.

Further, the present invention can be used for treating cancer by diverting or blocking blood flow to tumors, the present invention is particularly useful for treating tumors in areas that are not easily accessible for surgical intervention, for example, brain tumors.

Other advantageous uses of the present invention are for aortopulmonary closure; treatment of artery pseudoaneursym; hepatic artery vascular occlusion and for temporary vascular occlusion during co-administration of cytotoxic drugs; treatment of other types of vessels, for example, the composition can be used for creating tubal or vas deferens occlusion, and urinary occlusion.

Still another advantageous use is the controlling and smoothing the blood flow around stents. A major complication from the balloon angioplasty and the use of stents is disruption of the smooth flow of blood past and around the stent which can lead to the formation of blood clots and their associated complications. The composition of the present invention can be used to modify and make regular the slip streams of blood through and adjacent to the stent to mitigate or alleviate the cause of the turbulence, and such turbulence causing states.

Administration

The monomer component and polymer components are combined just prior to use. The composition is administered by a microcatheter, syringe or similar device capable of delivering a precise amount of the composition to a specifically desired location in the lumen of a vessel. Delivery can also be made with a microcatheter made from or coated with an agent that lessens the likelihood of accidental gluing of the device to the vessel, for example, hydrophilic coating and silicone derivative coatings.

EXAMPLES

The following examples are given to enable those of ordinary skill in the art to more clearly understand and to practice the present invention. The examples should not be considered as limiting the scope of the invention, but merely as be illustrative and representative thereof.

Example 1

Preparation of 2-Hexyl Cyanoacetate

A 5 liter, 24/40 ground glass jointed flask was configured with a reflux condenser, Dean-Stark trap, and football magnetic stirring bar. The reaction vessel was charged with the 1,275.0 g of cyanoacetic acid (Aldrich Chemical Co.), 1,581.5 g of 2-hexanol (Aldrich Chemical Co.) and 3.0 g of p-toluenesulfonic acid (Aldrich Chemical Co.), and 1,500 of toluene (Aldrich Chemical Co.). The reaction mixture was stirred and heated to reflux. Water was formed as a byproduct of the reaction and was collected during the course of the reaction. The reaction was continued until there was a period of over 30 minutes where no water was produced. The amount of water collected was 230 ml and indicated that the reaction had completed with a 85.2% theoretical yield. The reaction mixture was allowed to cool to room temperature.

The reaction mixture was stirred and 500 ml of a saturated baking soda (sodium bicarbonate) solution was gradually added to the mixture. The reaction mixture was stirred vigorously until the frothing stopped. The reaction mixture was poured into a six liter separatory funnel, to which an additional 500 ml of water was added. The funnel was vigorously agitated. The aqueous phase was separated and saved as Reaction Water. The pH of the aqueous layer was measured to insure that the pH was over 8. Another 500 ml of water was added to the organic phase reaction mixture in the separatory funnel. The contents of the funnel were again agitated, the aqueous and organic phases were allowed to settle, and the aqueous phase separated and also saved as Reaction Water. This washing procedure was repeated two additional times. The organic phase was moved to a 5-liter flask. The flask was configured with a distillation condenser. The reaction mixture was heated to reflux, and the remaining water was separated from the mixture and discarded. The apparatus was reconfigured for vacuum fractional distillation. Initially, the toluene and 2-hexanol in the mixture were removed by reducing the pressure of the apparatus to about 5 Torr, and then by heating the mixture to 60° with stirring. After the solvents were removed, the pressure was further reduced to less than 1 Torr and gradually increased heat until the desired 2-hexyl cyanoacetate began to distill off. The heat was adjusted so that the product was recovered at a rate of 2 drops/sec. The recovery collected 1921.1 g (70.76% yield) of the 2-hexyl cyanoacetate, and was halted when no more material came out of the distillation unit. Gas chromatographic analysis of the purity of the 2-hexyl cyanoacetate indicated that the product was 98.3% pure, which was well above 95% purity requirement for proceeding to the next procedure.

If the purity of the 2-hexyl cyanoacetate had been below 95%, the material could have be purified by vacuum distillation, or using any like technique for purification known to those of ordinary skill in the art.

Example 2

Preparation of 2-Hexyl Cyanoacrylate

A 5-liter three-necked flask was configured with a reflux condenser, Dean-Stark trap, an addition funnel and a mechanical stirrer with a glass paddle in a 5-liter heating mantle. Paraformaldehyde 272.4 g and methanol 1,500 ml were combined in the flask. The reaction mixture was heated to reflux and stirred for a period of 1 hr until the solution began to cleared. 3 ml of piperidine was washed into the reaction mixture with methanol, followed by 1521.9 g of 2-hexyl cyanoacetate added in a dropwise fashion. The resulting reaction was exothermic, and the heat was adjusted to maintain the reaction mixture at reflux temperature. The reaction mixture was refluxed for an additional 30 minutes after the conclusion of the addition. Methanol was distilled from the reaction mixture and collected through the Dean-Stark trap until 1420 ml of the original methanol (98%) was recovered (compensating for spillage). The reaction mixture was halted overnight at this point.

The reaction vessel was configured with a vacuum apparatus to collect residues, and placed under high vacuum to remove remaining volatile materials. The vacuum was gradually increased until less than 10 Torr was reached. The apparatus was heated until all the solvent had been removed. Once the solvent was removed, 100 g of phosphorus pentoxide was added to the mixture taking care to minimize its exposure to air. The heat was discontinued, and the mixture was stirred for one hour. The apparatus was then flooded with sulfur dioxide. The pressure was reduced to less than 10 Torr and heated slowly, the flow of sulfur dioxide was adjusted for a constant low-level flow of gas into the apparatus.

A 1 liter flask was washed with concentrated sulfuric acid, three times with water, and once with ultra pure water. The flask was oven dried for one hour at 110° C. and was allowed to cool to room temperature. 10 drops of 85% phosphoric acid and approximately 25–50 mg of hydroquinone was added to the 1 liter flask. The flask was fitted as the receiver flask to the distillation apparatus. The pressure of the distillation was reduced to less than 10 Torr. The reaction mixture was heated and stirred until the distillation began. 418 g of 2-hexyl cyanoacrylate was collected at a 25% yield. The distillation was halted when the temperature rose above 110° C.

Example 3

Purification of 2-Hexyl Cyanoacrylate

The 2-hexyl cyanoacrylate was purified in a two step process. The compound was first by vacuum distillation, and then further purified by spinning band column.

Vacuum Distillation

A vacuum distillation apparatus was configured with a 2 L flask, magnetic stirrer, fraction cutter, a 10" Vigreux column a clasien head, condenser, thermometer and a 100 ml forecut receiving flask. 10 drops of 85% phosphoric acid and 10 mg of hydroquinone was added to the forecut flask. The unpurified 2-hexyl cyanoacrylate was place into the distillation flask and the pressure of the unit was reduced to just under 1 Torr. The material was stirred and gradually heated until product was being distilled and collected at a rate of one drop per minute. After 35 ml of distillate was collected, a second 2 L receiving flask that had been prepared by acid washing, followed by the addition of 25 drops of 85% phosphoric acid and 20 mg hydroquinone was placed to receive the distillate. The distillation rate was gradually increase till the product was being collected at a rate of 2–3 drops per second. When the distillation head temperature rose 2° C. above that used to collect the main fraction, the distillation was completed. Heat was discontinued, and the material was allow to cool under dry air by air filtered through a drying tube.

Spinning Band Column Purification

The spinning band column (B/R Instrument Corp., 9119 Centreville Road, Easton, Md. 21601, Model 9600) is a long jacketed silvered column fitted with a 30/50 socket joint at the bottom. A magnetic stirring bar was added to the 5 L socket joint flask, which was then filled with the product to be purified. A heating mantle is supported on a magnetic stirrer that is raised and lowered with a laboratory jack to fit to the column. On the upper right hand side of the column there was another 30/50 male socket joint for a 100 ml receiving flask. All flasks and joints were greased with high vacuum grease to assure a good vacuum seal. When assembled, a glass temperature probe was inserted into the 10/15 joint of the flask, and a metal Tempora probe was inserted inside the glass probe. The 29/42 joint containing the stopcock was greased and placed into the flask and connected to a sulfur dioxide gas line. The pressure of the system was gradually reduced down to just under 1 Torr of pressure.

Operation of the spinning band column was controlled by a microprocessor. The column was programmed to operate under the following conditions, the water cooling temperature was set to 15° C., the column's motor turns on at 24° C., equilibration time was 2 min, open temperature 28° C., close temperature 90° C., mantle rate 24° C., reflux ratio 20 to 1 and pot temperature to end run 90° C. Just prior to beginning the distillation a small flow of sulfur dioxide was leaked into the system. The temperature of the flask was monitored during the distillation to ensure that the temperature at no time rose above 100° C. The distillate was collected in the receiver flask at the end of the distillation.

The contents in the flask of the spinning band column were allowed to cool for 30 min. A second high vacuum distillation apparatus configured identically to the vacuum distillation apparatus first used in this procedure was setup using a 2 L round bottom flask. To this flask was added 0.0269 g of hydroquinone, 0.0275 g of p-methoxyphenol, and 0.0794 g of phosphoric acid. The residue for pot of the spinning band column was added to the 2 L round bottom flask of the vacuum distillation apparatus. The contents of the flask was stirred and the pressure of the unit was reduced to just less than 1 Torr. A small stream of sulfur dioxide was leaked into the apparatus as the distillation continued. A receiver flask was prepared by adding 10 mg hydroquinone and 15 drops of 85% phosphoric acid. A forecut fraction of 86.3 g was collected at the rate of 2–6 drops per minute. The main fraction was collected in a receiver similarly prepared as the forecut fraction flask. 1620.1 g of main fraction product was collected at a rate of 20–25 drops per minute. The material was then re-distilled by the spinning band column under the previous conditions.

The purity of the 2-hexyl cyanoacrylate was determined by gas chromatography. The gas chromatograph was configured as follows, HP 5890 Gas Chromatograph with HP Chemstation Software.

| Column Description: | Supelco Nukol (60 meter, I.D.- 0.32 mm, film thickness- 1 micron). |
|---|---|
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 20 PSI |
| Aux: | 60 PSI |

-continued

| | |
|---|---|
| Initial Oven Temperature: | 140° C. for 20 min. |
| Ramp: | 5° C./min. |
| Final Oven Temperature: | 200° C. for 50 min. |
| A Splitless System. | |
| Injection Volume: | 1.0 micro liter |

1.0069 g of the 2-hexyl cyanoacrylate was mixed thoroughly with 2 drops of 1-hexanol (0.0044 g), was analyzed and impurities were found to be at an acceptable for use. The 2-hexyl cyanoacrylate was sufficiently pure to use for product.

Example 3

Formulation of the Monomer Component

The monomer component was formulated with the following materials 2-hexyl cyanoacrylate 1249.9 g, hydroquinone 0.0764 g, p-methoxyphenol 0.0874 g and phosphoric acid 0.1693 g. The hydroquinone and p-methoxyphenol were kept under reduced pressure in a dessicator over a drying agent. The pure phosphoric acid was particularly deliquesent and care was taken not permit water contamination. The calculated molar quantities and PPM of each material were as follows,

| Material | Moles | PPM |
|---|---|---|
| 2-hexyl cyanoacrylate | 6.8964 | 999,547 |
| hydroquinone | 0.000694 | 100 |
| p-methoxyphenol | 0.000704 | 102 |
| phosphoric acid | 0.001726 | 250 |

Overall purity of the formulation was determined by gas chromatograph to be less than 1%, using 1-hexanol as an internal standard.

| | |
|---|---|
| Instrument Description: | HP5890 Gas Chromatograph with HP chemstation software. |
| Column Description: | Supelco Nukol (60 meters-length, I.D., 0.32 mm, Film Thickness 1 micron) |
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 40 PSI |
| Aux.: | 60 PSI |
| Initial Oven Temperature: | 140° C. for 20 min. |
| Ramp: | 5° C./min. |
| Final Oven Temperature: | 200° C. for 50 min. |
| A Splitless System: | |
| Injection Volume: | 1.0 microliter |

Example 4

Preparation of the 2-Hexyl Cyanoacrylate Polymer Component

Ethyl myristate was obtained commercially from Aldrich Chemical Company at 97% purity. Prior to use, the ethyl myristate was further purified by vacuum distillation to 99.8% purity following standard routine chemical procedures.

Six 3 ml syringes were fill with purified 2-hexyl cyanoacrylate. 500 mg of sodium bicarbonate and 250 ml of ultra pure water were placed into a Waring blender. The lid of the blender was adjusted so that the contents of the syringes could be emptied dropwise into the center of blender while the blender was stirring. With the speed of the blender set to high, each of the syringes were emptied in a dropwise fashion into the stirring blender. When the addition was completed, the lid of the blender was closed and the mixture was stirred for another minute. The solution was decanted from the blender leaving just solid material in the blender. Residual solid material that was inadvertently removed with the decanted solution was recovered by filtration, washed with ultra pure water and placed back into the blender. An solid material adhering to the inside portion of the blender was rinsed with ultra pure water back with the rest of the solids in the blender. An additional 250 ml of ultra pure water was added into the blender, and the water and solid mixture was blended for 1 minute. The process of decanting the water, and recovering separate solid material followed by addition of ultra pure water and blending was repeat two more times. Following the last procedure, water solution was decanted through a large coarse fritted glass funnel filter that recovered solid material in the solution. The solid material collected by the filter was washed with methanol prior to be added back to the rest of the solid material. The walls of the blender were rinsed with methanol to collect all the solid material back into the blender. 250 ml of Methanol was added to the blender. The solids were blended for one minute. The solid material is filtered from the methanol. Any residual solid material in the blender is washed with methanol and combined with the solid material filtered from the methanol. The solid material on the filter was placed under a low vacuum to remove the rest of the methanol. The solid material was moved quantitatively to a 100 ml round bottom standard tapered flask. The flask was placed under reduced pressure to remove the remaining methanol. 2 g of the solid material was combined with 100 g of powdered gold. The mixture was placed into a standard laboratory blender and blended for one minute. The blender was agitated constantly during the blending to ensure that the gold did not settle during the blending. 1.020 g portions of the blended material were placed into previously cleaned and prepared bottles. To each bottle was added 500 mg of ethyl myristate at 99.8% purity. The filled bottles were kept under a Laminar flow hood. The unsealed bottles were arranged in trays for immediate ethylene oxide sterilization by Sharp Coronado Hospital, Sterile Processing Department under standard conditions.

Example 5

Comparison of Cathether Adhesion Force for 2-Hexyl Cyanoacrylate (Neuracryl M) and n-Butyl Cyanoacrylate (Histoacryl) Compositions The present invention is also known by the name of Neuracryl M, where Neuracryl M1 corresponds to the monomer component, and Neuracryl M2 corresponds to the second component comprising of the gold coated 2-hexyl acrylate. This example demonstrates differences in adhesion between the two cyanoacrylates by measuring the amount of force required to remove a catheter from various compositions of Neuracryl and Histoacryl. Histoacryl is commercially available from Braun GmbH. It is similar to Neuracryl M in that it is a polymer composition also based on a cyanoacrylate structure, i.e., n-butyl cyanoacrylate. However, the force required to withdraw a catheter from Histoacryl is greater than that required for Neuracryl M, and in this key aspect, Neuracryl M possesses a surprising and unexpected advantage over Histoacryl.

The force resulting from catheter adhesion was determined for Neuracryl M1 and M2 (mixed), pure Neuracryl M1, Neuracryl M1 mixed with 33% Ethiodol, Neuracryl M1 mixed with 50% Ethiodol, pure Histoacryl, Histoacryl mixed with 33% Ethiodol, and Histoacryl mixed with 50% Ethiodol were measured and compared.

All the mixtures were injected through a TurboTracker microcatheter device (Medi-tech/Boston Scientific, Watertown, Mass.). All mixtures were prepared immediately prior to use to prevent separation of the components or contamination. The catheter tips were placed at the bottom of 10 mm deep by 5 mm diameter wells filled with 0.2 mL of heparinized human whole blood. Through the microcatheter, 0.15 mL of each embolic mixture was injected into each well, surrounding the tip of the microcatheter. Mixtures containing Histoacryl were allowed to polymerize for 1 minute, and those containing Neuracryl for 3 minutes. The microcatheters were then extracted from the polymerized cyanoacrylates at a constant speed of 8.3 mm/sec (Model 1000 Materials Testing System; Instron, Canton, Mass.) and the forces required for extraction were measured and recorded (Minibeam Force Transducer, 25-lb capacity; Interface Advanced Force Measurement, Scottsdale, Ariz.). Five samples of each mixture were tested. Comparison of the results was performed using the Student t test.

Successful mesurements of the peak forces required for the extraction of the catheters from the polymerized cyanoacrylates were obtained for six of the seven mixtures tested. A wide range of peak forces were required to extract the microcatheters from the various mixtures. The force of extraction for the Neuracryl M1 and 50% Ethiodol mixture was less than 0.05 Newtons and beyond the ability of the apparatus to obtain precise measurements. The peak forces required to extract the microcatheters from either Histoacryl mixed with 33% Ethiodol (1.44 N±0.33) were significantly higher ($P<0.01$; $P<0.05$) than those for pure Neuracryl M1 (1.00N±0.23). Histoacryl had to be mixed with 50% Ethiodol to decrease the force of extraction (0.34N±0.14) to less than that associated with pure Neuracryl M1 ($P<0.01$).

When Neuracryl M1 and M2 were mixed together the force required for microcatheter extraction (0.41N±0.14) was significantly lower than that for either pure Histoacryl (1.83 N±0.21), Histoacryl mixed with 33% Ethiodol (1.44 N±0.33), or Neuracryl M1 alone (1.00 N±0.23) ($P<0.01$; $P<0.01$; $P<0.01$, respectively). The force required to extract microcatheters from the Neuracryl M1 and M2 mixture was not, however, significantly different from that of Histoacryl mixed with 50% Ethiodol (0.41 N±0.14 vs. 0.34 N±0.14).

Although Neuracryl M1 was not designed to be mixed with Ethiodol, like Histoacryl, Neuracryl M1 demonstrated markedly decreased microcatheter adhesion when mixed with 33% and 50% Ethiodol. The extraction force was reduced significantly from 1.00 N±0.23 to 0.28 N±0.12 when Neuracryl M1 was mixed with 33% Ethiodol ($P<0.01$). There was no significant difference between the peak extraction forces for Neuracryl M1 mixed with 33% Ethiodol and Neuracryl M1 and M2 mixed was intended for clinical use. (0.28 N±0.12 vs 0.41 N±0.14). When Neuracryl M1 was mixed with 50% Ethiodol, the force of extraction was less than 0.05 N and below our limit for accurate measurement. The force was so low that, unlike with the other mixtures, no effacement of the slight natural curve of the catheter was observed prior to the tip of the catheter pulling out of the cyanoacrylate.

Example 6

Comparison of 2-Hexyl Cyanoacrylate and n-Butyl Cyanoacrylate Interactions with Blood and in an Arteriovenous Malformation Model The following example compares the interaction of 2-hexyl cyanoacrylate composition of the present invention (2HCA) and a composition of 33% n-butyl cyanoacrylate and 66% ethiodol (NBCA), which is the clinical standard, with blood.

2HCA was compared to NBCA in heparinized pig blood under four conditions:

(1) a drop of each composition was placed on the surface of blood, observed, and the polymerization process was timed.

(2) a 22 gauge needle was placed below the surface of static blood, and 0.4 milliliter of each composition was injected and observed over a 1 minute period;

(3) blood was circulated through a 4 millimeter I D polyvinyl chloride tubing at 40 centimeters per second. A 22 gauge needle inserted into the central slipstream introduced the compositions at rates varying from 0.1 ml to 8 ml per second powered by a Medrad mk 4 pressure injector. Behaviors were recorded via fluoroscopy on S VHS T V;

(4) standardized arteriovenous malformation models were placed in a circuit of pulsatile flowing blood, and the compositions were introduced via microcatheters under direct fluoroscopic control, using the same techniques used in humans. The models were later opened, the polymerized compositions were removed and their characteristics were compared. Polymer which escaped from the models were also collected downstream and examined.

Findings:

(1) Dropping the compositions onto the surface of blood yielded generally equal polymerization times, about 2 seconds.

(2) When injected below the surface of static blood, the 2HCA formed a rubbery elastic mass which remained at the needle's tip. The NBCA compound fell away from the needle, to the bottom of the beaker and polymerized to a friable mass.

(3) When injected into blood flowing at physiologic velocities, the NBCA compound formed small, individual, nearly spherical droplets that did not remain as a cohesive mass, but rather broke away and embolized down stream. There was no injection rate at which we could keep the device from embolizing away, or to make it block the tube. Conversely, there was no rate of injection which could prevent the 2HCA from remaining as a cohesive polymerized mass and the tube was blocked solidly for the length of the injection.

(4) When injected into the AVM model, the 2HCA yielded significantly better penetration than the NBCA compound. The character of the polymerized compositions was significantly different: the NBCA compound made a firm yet friable mass much like dry cottage cheese; the 2HCA mass was elastic much like chewing gum.

In summary, the standard test of the cyanoacrylate drop on blood yielded no predictive information. However, when the cyanoacrylates were respectively injected below blood, strikingly different outcomes were observed. The NBCA immediately fell away from the needle to the bottom of the beaker, whereas the 2HCA remained as a cohesive whole at the needle tip. There was no introduction rate which could disrupt the cohesiveness of 2HCA; there was no introduction rate which allowed the NBCA composition to remain a cohesive whole. Particles of the NBCA composition formed and continually pushed downstream. Injection of 2HCA into standard AVM models yielded consistently better control penetration of the nidus of the AVM.

We claim:

1. A composition useful as an embolic agent that selectively creates an embolic blockage in the lumen of a blood vessel, duct, fistula or other body passageways comprising combination of a monomer component and a second component, wherein, said monomer component comprises a 2-hexyl cyanoacrylate monomer and at least one inhibitor agent; and said second component comprises an opacificant agent and a plasticizer.

2. The composition of claim 1, wherein the second component is an iodinated oil.

3. The composition of claim 2, wherein said iodinated oil is 37% iodine by weight, covalently linked to the fatty acids of poppy seed oil.

4. The composition of claim 1, wherein the second component is a brominated oil.

5. A composition useful as an embolic agent that selectively creates an embolic blockage in the lumen of a blood vessel, duct, fistula or other body passageways comprising a 2-hexyl cyanoacrylate monomer and at least one inhibitor agent, a polymer resulting from said 2-hexyl cyanoacrylate monomer, an alkyl esterified fatty acid and an opacificant agent.

6. The composition of claim 5, wherein there are at least three inhibitor agents.

7. The composition of claim 6, wherein said inhibitor agents are hydroquinone, p-methoxyphenol and phosphoric acid.

8. A composition useful for selectively creating a polymeric blockage in the lumen of a vessel comprising combination of a monomer component and a polymer component, wherein said monomer component comprises, 2-hexyl cyanoacrylate monomer, hydroquinone, p-methoxyphenol and phosphoric acid; and said polymer component comprises, 2-hexyl cyanoacrylate polymer, gold, and ethyl myristate.

9. The composition of claim 8, wherein hydroquinone is present in the range of about 50 to 150 PPM of 2-hexyl cyanoacrylate.

10. The composition of claim 8, wherein p-methoxyphenol is present in the range of about 50 to 150 PPM of 2-hexyl cyanoacrylate.

11. The composition of claim 8, wherein phosphoric acid is present in the range of about 125 to 375 PPM of 2-hexyl cyanoacrylate.

12. The composition of claim 8, wherein hydroquinone is present in the range of about 75 to 125 PPM of 2-hexyl cyanoacrylate.

13. The composition of claim 8, wherein p-methoxyphenol is present in the range of about 75 to 125 PPM of 2-hexyl cyanoacrylate.

14. The composition of claim 8, wherein phosphoric acid is present in the range of about 187.5 to 312.5 PPM of 2-hexyl cyanoacrylate.

15. The composition of claim 8, wherein hydroquinone is present in the range of about 95 to 105 PPM of 2-hexyl cyanoacrylate.

16. The composition of claim 8, wherein p-methoxyphenol is present in the range of about 95 to 105 PPM of 2-hexyl cyanoacrylate.

17. The composition of claim 8, wherein phosphoric acid is present in the range of about 200 to 300 PPM of 2-hexyl cyanoacrylate.

18. The composition of claim 8, wherein hydroquinone is present in the range of about 100 PPM of 2-hexyl cyanoacrylate.

19. The composition of claim 8, wherein p-methoxyphenol is present in the range of about 100 PPM of 2-hexyl cyanoacrylate.

20. The composition of claim 8, wherein phosphoric acid is present in the range of about 250 PPM of 2-hexyl cyanoacrylate.

21. The composition of claim 8, wherein hydroquinone is present at about 100 PPM of 2-hexyl cyanoacrylate, p-methoxyphenol is present at about 100 PPM of 2-hexyl cyanoacrylate and phosphoric acid is present at about 250 PPM of 2-hexyl cyanoacrylate.

22. A method of selectively creating an embolic blockage in the lumen of a blood vessel, duct, fistula or other body passageways comprising administration of the composition of claim 1 with a device capable of delivering a precise amount to the lumen of a blood vessel, duct, fistula or other body passageway.

23. A method of treating arteriovenous malformation comprising administration of the composition of claim 1 with a device capable of delivering a precise amount to the malformation.

24. A method of treating arteriovenous malformation comprising administration of the composition of claim 5 with a device capable of delivering a precise amount to the malformation.

25. A method of treating arteriovenous malformation comprising administration of the composition of claim 8 with a device capable of delivering a precise amount to the malformation.

* * * * *